United States Patent [19]

Wickham

[11] Patent Number: 5,531,898
[45] Date of Patent: Jul. 2, 1996

[54] SEWAGE AND CONTAMINATION REMEDIATION AND MATERIALS FOR EFFECTING SAME

[75] Inventor: Daniel E. Wickham, Sebastopol, Calif.

[73] Assignee: International Organic Solutions Corp., Mill Valley, Calif.

[21] Appl. No.: 418,589

[22] Filed: Apr. 6, 1995

[51] Int. Cl.$^6$ .................. C02F 3/34; C12N 9/00
[52] U.S. Cl. ............. 210/606; 210/611; 210/613; 210/622; 210/631; 210/632; 435/187; 435/188; 435/262.5
[58] Field of Search ................. 210/606, 601, 210/609–613, 620, 622, 630–632; 435/187, 188, 222, 252.34, 252.5, 262.5, 267, 821, 839, 876

[56] References Cited

U.S. PATENT DOCUMENTS

| | | | |
|---|---|---|---|
| 3,105,041 | 9/1963 | Genter et al. | 210/6 |
| 3,717,550 | 2/1973 | Ziffer | 195/63 |
| 3,824,186 | 7/1974 | Erickson et al. | 210/7 |
| 3,877,920 | 4/1975 | Carlberg | 71/21 |
| 4,132,638 | 1/1979 | Carlson | 210/7 |
| 4,385,121 | 5/1983 | Knowlton | 210/611 |
| 4,457,945 | 7/1984 | Imamura et al. | 71/5 |
| 4,468,461 | 8/1984 | Bopp | 210/611 |
| 4,582,607 | 4/1986 | Kiese et al. | 210/612 |
| 4,663,044 | 5/1987 | Goronszy | 210/610 |
| 4,721,585 | 1/1988 | Santolini et al. | 210/631 |
| 4,791,063 | 12/1988 | Hou et al. | 435/243 |
| 4,853,334 | 8/1989 | Vandenbergh et al. | 435/262 |
| 4,859,594 | 8/1989 | Portier | 210/601 |
| 4,882,059 | 11/1989 | Wong et al. | 210/606 |
| 4,936,994 | 6/1990 | Wiatr | 210/632 |
| 4,936,996 | 6/1990 | Messing | 210/611 |
| 4,943,530 | 7/1990 | Christner et al. | 435/188 |
| 4,952,229 | 8/1990 | Muir | 71/7 |
| 4,994,390 | 2/1991 | Wiatr | 435/262 |
| 5,037,758 | 8/1991 | Mulligan et al. | 435/252.5 |
| 5,068,036 | 11/1991 | Li et al. | 210/606 |
| 5,141,646 | 8/1992 | Rozich | 210/613 |
| 5,188,956 | 2/1993 | Nanmori et al. | 435/200 |
| 5,227,067 | 7/1993 | Runyon | 210/606 |
| 5,271,845 | 12/1993 | Paquin | 210/606 |
| 5,284,587 | 2/1994 | Wong et al. | 210/606 |
| 5,312,749 | 5/1994 | Griffin et al. | 435/220 |
| 5,314,619 | 5/1994 | Runyon | 210/606 |
| 5,324,432 | 6/1994 | Robertson et al. | 210/632 |
| 5,336,290 | 8/1994 | Jermstad | 71/13 |
| 5,364,789 | 11/1994 | Guinn et al. | 435/262.5 |
| 5,464,766 | 11/1995 | Bruno | 435/187 |

FOREIGN PATENT DOCUMENTS

| | | | |
|---|---|---|---|
| 3806820A1 | 9/1989 | Germany | 435/262.5 |
| 3816679A1 | 11/1989 | Germany . | |
| 51-13165 | 2/1976 | Japan | 210/610 |
| 54-98047 | 8/1979 | Japan | 210/616 |
| 51-36598A | 2/1984 | Japan | 210/601 |
| 59-39391 | 3/1984 | Japan | 210/620 |
| 61-78494 | 4/1986 | Japan . | |
| 61-20356 | 5/1986 | Japan | 210/620 |

OTHER PUBLICATIONS

Stay et al., Enzyme Activated Bioremediation of Contaminated Soils, Pacific Basin Conference on Handling of Hazardous Waste, 1–11, 1991.

(List continued on next page.)

Primary Examiner—Thomas G. Wyse
Attorney, Agent, or Firm—Laff, Whitesel, Conte & Saret, Ltd.

[57] ABSTRACT

Methods for the biological treatment of sewage in a sewage treatment plant, of wastestreams and of ponds are disclosed. The methods employ a composition comprising active amounts of an enzyme mixture, *B. subtilis* and *P. fluorescens*, and a nutrient source having a COD of 10,000 mg/kg or less, of which one source is used mushroom compost. The composition is first activated in fresh water, is then acclimated in a waste moiety, and the acclimated mixture is then used to treat the main body of the waste, such as sewage sludge, a wastestream or a pond.

27 Claims, 1 Drawing Sheet

OTHER PUBLICATIONS

Wickham et al., Enzyme Activated Composting for Bioremediation of Contaminated Soils, Proceedings of National Research & Development Conference on the Control of Hazardous Materials, 326–329, 1991.

Shamala, Degradation of stachy substrates by a crude enzyme preparation and utilization of the hydrolyzates for lactic fermentation—using Aspergillus ustus enzyme preparation and Lactobacillus plantarum fermentation; lactic acid production, Abstract from Enzyme Microb. Technol. (9, 12, 726∝29), 1987.

Tan, Screening for extracellular enzymes of fungi from manufacturing wastes, Abstract from Mircen J. Appl. Microbiol. Biotechnol., 2 (4), 445–452, 1986 (Recd. 1987).

Tan, Screening for extracellular enzymes of fungi from manufacturing wastes—production of cellulase, protease, amylase and lipase using fungus from brewery spent grain, sesame seed meal and soybean meal wastes, Abstract from Mircen J. Appl. Microbiol. Biotechnol., (2, 4, 445–52), 1986.

Mishra, Origin and Distribution of digestive enzymes in soldiers of neotermes–bosei snyder with a note on gut morphology isoptera kalotermitidae, Abstract from Mater Org (BERL) 22 (2), 127–138, 1987.

Manonmani et al., Saccharification of sugar–cane bagasse with enzymes from Aspergillus ustus and Trichoderma viride—determination of optimum chemical pretreatment and incubation conditions, Abstract from Enzyme Microb. Technol. (9, 8, 484–88), 1987.

McLean et al., A preliminary investgation of extracellular enzyme production by some species of Aspergillus, Abstract from S. Afr. J. Bot., vol. 51, (6), 425∝31, 1985.

Two abstracts of Japanese Patent 60137888 (kokai), Jul. 22, 1985.

Two abstracts of Japanese Patent 60137887, Jul. 22, 1985.

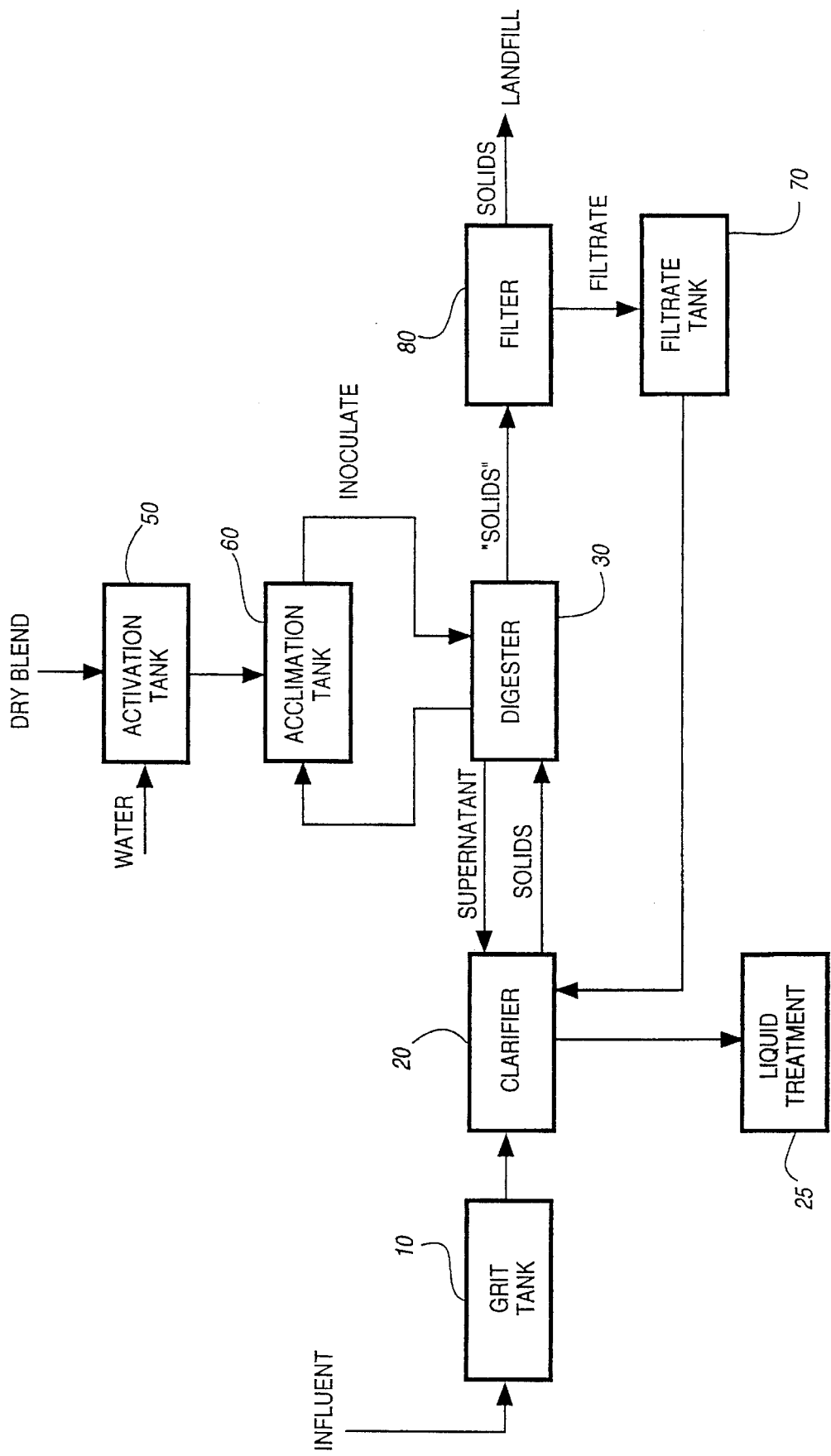

SEWAGE AND CONTAMINATION REMEDIATION AND MATERIALS FOR EFFECTING SAME

BACKGROUND OF THE INVENTION

For many years it has been known to be desirable to dispose of waste in a sanitary form. More recently, the use of selected biological materials to treat waste and to remediate contamination or spills and the like has made it possible to improve the efficiency of such disposal and remediation. A wide variety of such biological materials and techniques for their use are available.

Efforts have gone into providing improved biological materials for use in waste disposal and remediation techniques, into providing improved techniques for waste disposal and remediation, and into providing improvements in sewage treatment.

Sewage is the spent water supply of a community. Typically it is about 99.95% water and about 0.05% waste material and has a high biochemical oxygen demand (BOD). Raw sewage is generally comprised of water and suspended solids, consisting of both organic materials and inorganic materials. When the raw sewage enters a sewage treatment plant, the total suspended solids (TSS) may typically be about 300 ppm. During treatment in sewage treatment plants, the solids are concentrated and separated from the water, and the water and solids are treated and disposed of separately.

Organic materials make up most of the total suspended solids (TSS) in the raw sewage. Such organic materials include, as significant components, celluloses; proteins; lipids (fats); and starches, including amyloses and amylopectins. Other organic materials may include lignins, nucleic acids, hemicelluloses, and various other polysaccharides and polymers. Most of these organic materials comprise large molecules which results in much of the suspended solids being colloidal in nature, although some of the organic materials may also be in dissolved form or in particulate form.

The organic material also includes various microorganisms, such as bacteria, algae, and fungi, which feed on the organic materials. Some of these microorganisms exude still more large molecules, creating slime and other environmentally undesirable materials.

Inorganic materials make up a relatively small amount of the TSS, generally less than 15 to 20% of the TSS.

In a sewage treatment plant, raw sewage is usually first introduced to a tank, such as an aerated grit tank, in which very large solids, such as T-shirts, shoes, and other such undesirable materials and objects, are allowed to settle out. These very large solids are typically taken to a landfill without further significant treatment.

The remainder of the raw sewage is then treated to become acceptable to reintroduce to the environment. To that end the raw sewage goes through a second settling and clarifying process in clarifiers, in which a solids moiety (the aqueous sludge) is separated from the majority of the liquid (the supernatant). The supernatant is removed from the clarifiers for further treatment, such as chlorination, to sanitize the liquid. Before the supernatant may be reintroduced to the environment, its BOD must decline to acceptable levels, often as specified by government regulations. The sanitized supernatant is eventually reintroduced to the environment.

The solids moiety, which is typically about 3 to 4% solids in liquid, is introduced into a thickener tank for settling or to a digester, in which endogenous enzymatic and microbial activities are traditionally used to reduce the solids somewhat. Generally, the solids are held in the digester for a residence time of from at least two days to the preferred minimum of seven days, and up to 10 to 20 days, to allow the endogenous enzymes and microbes to act on the suspended solids.

Supernatant is gradually removed from the digester as digestion progresses and is recycled to the clarifiers. Solids are eventually removed from the digester and are dewatered via a centrifuge or filtering, creating a cake. The cake is removed to a landfill, is applied to farmland, or is incinerated. The cake is typically about 15% to 30% TSS, and about 85% to 70% water.

In typical prior art digestion methods of the type described, endogenous enzymes and microbes are usually slow and inefficient at reducing the TSS. Thus, significant amounts of solids must be removed from the digesters and sewage treatment plants and must be disposed of at great expense and in conformance with governmental guidelines. Some municipalities spend more than $100 per ton to dispose of such solid waste.

Treating the suspended solids and preparing the solids for final disposal is one of the most expensive components of sewage treatment. It can also be the limiting step in determining the volume of raw sewage which may be treated in a sewage treatment plant. Thus, if a plant is running near capacity, decreasing the solids produced may delay the need for a new plant or additional digesters. Therefore, if it were possible to decrease the amount of solids to be treated and disposed of, this would reduce both incremental costs and could eliminate the need for capital investment in many situations.

SUMMARY OF THE INVENTION

In accordance with the present invention an improved method of treating sewage at a sewage treatment plant is provided. In addition, improved biological materials for carrying out that method are provided as well.

In one form of the invention a method for the continuous biological treatment of sewage to reduce the volume of aqueous sludge in a sewage treatment plant is provided and comprises the steps of:

(A) providing a mixture comprising (1) active amounts of an enzyme mixture comprising amylase, lipase, protease, and cellulase; (2) active amounts of bacteria comprising *Bacillus subtilis* and *Pseudomonas fluorescens*; and (3) a nutrient source having a chemical oxygen demand of 10,000 mg/kg or less;

(B) immersing the mixture in water for from about 6 hours to about 48 hours at a temperature of at least 60° F. to produce an activated mixture;

(C) mixing a volume of aqueous sludge from the sewage treatment plant with a volume of the activated mixture for from about 6 hours to about 48 hours at a temperature of at least 60° F. to produce an acclimated mixture; and (D) adding a volume of the acclimated mixture of step (C) to a sludge treatment tank in the sewage treatment plant and maintaining the mixture and the sludge in contact at a temperature of at least 60° F. for at least two days to reduce the volume of aqueous sludge and suspended solids in the sewage treatment plant.

Preferably the method is carried out without aeration and steps (B) to (D) are repeated regularly, thereby to reduce and maintain a reduced volume of aqueous sludge and suspended solids in the sewage treatment plant. In a preferred form steps (B) through (D) are repeated to provide additional volumes of acclimated mixture for addition to the sludge treatment tank, each time using a reserved part of an acclimated mixture for production of each additional volume of acclimated mixture, and the volume of aqueous sludge of step (C) is taken from a sludge digester in the sewage treatment plant. Most desirably the temperatures in steps (C) and (D) are between about 90° F. and about 100° F.

In a preferred form, the quantity of the mixture added to water for activation is decreased over time. Once a steady state is reached, the amount of the mixture used per unit time may be substantially decreased to maintain the steady state condition.

The nutrient source preferably comprises used mushroom compost. Alternatively it may comprise a mixture of composted cow-paunch, composted mushroom stems, powdered kelp, and worm castings.

In another more general form of the invention, a method for the continuous biological treatment and purification of a wastewater stream containing organic contaminants is provided and comprises the steps of:

(A) providing a mixture comprising (1) active amounts of an enzyme mixture comprising amylase, lipase, protease, and cellulase; (2) active amounts of bacteria comprising *Bacillus subtills* and *Pseudomonas fluorescens*; and (3) a nutrient source having a chemical oxygen demand of less than about 10,000 mg/kg;

(B) immersing the mixture in water for from about 6 hours to about 48 hours at a temperature of at least 60° F. to produce an activated mixture;

(C) mixing a volume of the activated mixture with a volume of wastewater from the stream for from about 3 hours to about 48 hours, but more preferably at least about 6 hours, at a temperature of at least about 60° F. to produce an acclimated mixture; and (D) adding acclimated mixture of step (C) to the wastewater stream to reduce the organic contaminants.

The wastewater stream may be generated during the processing of one of the group consisting of wood, pulp, paper, chemicals, petrochemicals, pharmaceuticals, textiles, glues, foodstuffs, milk, coffee, eggs, meat, beef, chicken, fish, beer and wine. Preferably step (B) is conducted without aeration and the nutrient source comprises used mushroom compost.

A composition in accordance with the present invention for use in treating waste and contaminants preferably comprises an enzyme mixture comprising active amounts of amylase, lipase, protease, and cellulase; bacteria comprising active amounts of *Bacillus subtilis* and *Pseudomonas fluorescens*; and used mushroom compost. The used mushroom compost has desirably been previously used to grow at least two crops of mushrooms.

Further objects, features and advantages of the present invention will become apparent from the following description and drawings.

BRIEF DESCRIPTION OF THE DRAWINGS

FIG. 1 is a schematic showing of a typical sewage treatment plant in which the method of the present invention may be employed.

DETAILED DESCRIPTION OF THE INVENTION

In one aspect of the present invention, raw sewage is treated so that the organic solids content is substantially reduced, without increasing residence time in the plant or in the digesters, thereby reducing disposal costs and increasing the effective capacity of a sewage treatment plant.

As shown by FIG. 1, raw sewage or influent typically passes through an aerated settling tank, such as a grit tank 10, from which large solids, such as t-shirts, shoes and other large undesirable items, are removed in a conventional way for conventional treatment and disposal. The remaining raw sewage is then introduced into conventional separating tanks, such as clarifiers 20, for separation into liquid and solid moieties. The liquid moiety or component (the supernatant) is withdrawn for further treatment, such as by chlorination or by other conventional techniques as in a liquid treatment unit 25 to prepare it for return to the environment. The solids moiety or component (the aqueous sludge) which contains a substantial amount of organic material suspended in liquid, much of it colloidal, is then introduced into an existing or conventional digester 30.

In accordance with the present invention, it is into this same digester 30 that specially prepared biological materials are introduced. To that end, a dry blend of biological materials is provided for activation and eventual introduction into the digester to substantially reduce the TSS and to substantially reduce the solids produced by the plant and requiring disposal.

The preferred dry blend comprises a mixture of the bacteria *Pseudomonas fluorescens* and *Bacillus subtilis*; enzymes, including proteases, lipases, amylases, and cellulases; and used mushroom compost as a nutrient source. This preferred blend is referred to herein as Dry Blend A.

The used or spent mushroom compost is generated by growing at least one crop of mushrooms, but preferably two, on commercially available composted horse manure. Because horses, although herbivores, are not ruminants, their manure is made up of mostly of coarse, undigested plant material generally cellulosic in nature. Mushrooms, as fungi, are decomposers. As decomposers, they attack and digest the organic matter, such as horse manure, on which they are grown. Digestion is facilitated by secreting digestive enzymes, including cellulases and ligninases.

Although commercially used mushroom compost on which the mushroom *Agaricus bisporus* has been grown is preferably used, other used mushroom compost, such as that on which the shiitake mushroom *Lentinus edodes* has been grown, is believed to be suitable. After two crops are harvested, commercial mushroom growers consider the compost to be sufficiently exhausted of nutrients that they are no longer suitable for supporting commercial mushroom growth. Additionally, other fungal contaminants may become established on the compost, effectively competing with the mushroom crop for any remaining nutrients. This competition also adversely affects the size of the mushroom harvest.

Tests to determine the chemical oxygen demand (COD) confirm that the available nutrients in used mushroom compost have sharply declined from the level in the original horse manure. COD is defined by *Grant & Hackh's Chemical Dictionary* (1987) as:

a chemical measure of the deoxygenating power of the effluent in terms of the amount of oxidizing agent (e.g., boiling acidic potassium dichromate) reduced. More comprehensive oxidation is achieved than in the BOD test. COD ranges from 2 to 5 times BOD, depending on effluent composition.

Biochemical Oxygen Demand (BOD) is defined by *Grant & Hackh's Chemical Dictionary* (1987) as:

a chemical measure of the deoxygenating power of an effluent in terms of the difference between the dissolved oxygen content before and after 5 days at 20° C.

BOD is sometimes used as an index of the food value of wastewater.

In order to quantify COD of several composts, measured amounts of dried and ground organic material from various sources were infused in water for twenty-four hours. The COD was then determined via light absorption at 620 nm. The organic material infusions were measured against a standard solution with a COD of 150 mg/1. The following test results were obtained:

| Material | COD (mg/kg) |
| --- | --- |
| Used mushroom compost | 7,400 |
| Compost (commercially available) | 13,000 |
| Composted manure (commercially available) | 14,400 |

Using COD as a guide to the amount of food available for fungi or other decomposers such as bacteria indicates that used mushroom compost has substantially less food available than other composts. Experimentation has shown that typical commercially prepared composts have much higher COD measures, and are, therefore, unsuitable for use in the practice of the improved sewage treatment process of the present invention.

As mentioned, the compost used to support the mushroom crops is usually composted horse manure, but other organic matrices on which mushrooms have been grown may be suitable as well. For example other such used mushroom composts may be specially aged oak on which shiitake mushrooms are grown by individuals, and various soils, trees, fallen wood, and the like on which wild mushrooms are found.

Once the mushrooms are mature, the spore-producing bodies or basidiocarps of the mushrooms are harvested. The harvesting leaves the mycelia in the compost. The compost is prepared for use by screening and air drying to a moisture content of about 20 to 25% and is then ready to be blended with the enzymes and bacteria. The dried used mushroom compost is stable at room temperature and at low humidity substantially indefinitely.

The other components of the Dry Blend A are the bacteria, $P.$ $fluorescens$ and $B.$ $subtilis$, and enzymes, including a mixture of proteases, lipases, amylases and cellulases. $B.$ $subtilis$ is an aerobe, thriving at temperatures above about 90° F. $P.$ $fluorescens$ is a facultative anaerobe and is cold tolerant.

In a preferred embodiment of preparing the Dry Blend A, $P.$ $fluorescens$ and $B.$ $subtilis$, optionally with other genera of bacteria present, are first grown under conditions to stimulate extracellular secretion of the digestive enzymes in one of a variety of ways known to those who produce such enzymes commercially. It has been found experimentally that protease secretion is relatively unpredictable. Therefore, once the other enzymes and the bacteria have reached a level of effectiveness, the bacteria and enzymes are concentrated and dried, and protease is added in a dry form so that there is at least 1% protease, 1% cellulase, and 1% amylase by weight, as well as active amounts of lipase, in the final blend of bacteria and enzymes. Urea and $CaCl_2$ are added to the blend as a nutrient and a desiccant. These and the bacteria and enzymes are then subjected to freeze-drying and the freeze-dried mixture is milled to a fine powder.

The dried enzyme/bacteria blend is stable at room temperature substantially indefinitely. The dried, milled enzyme/bacteria blend is mixed with the dried used mushroom compost such as in a ratio of one part of blend to twenty parts of compost to form Dry Blend A. This mixture is also stable at room temperature and low humidity substantially indefinitely.

An alternative nutrient source material comprises a mixture of cow-paunch or rumen, mushroom stems, powdered kelp, and worm castings. Enzymes and bacteria similar to those previously described are added to this nutrient source, creating a blend of biological materials referred to herein as Dry Blend B. Dry Blend B was previously marketed for organic soil remediation and composting under the name BioCure. The COD of BioCure has been determined to be 7,200 mg/kg using the COD determination methods described above. The components of BioCure were described in a brochure dating from about 1983 as containing "a dry bacterial agar containing cultured activated enzymes in a dormant form", $Pseudomonas$ $fluorescens$, and $Bacillus$ $subtilis$. The ratio of the components was described as 65% biological cultures in a medium of composted waste materials, 25% activated enzymes from natural sources, 5% kelp, 5% inert.

The cow rumen of the nutrient source material was obtained from a slaughterhouse with contents more-or-less intact. The rumen is where microbes digest and ferment swallowed food, breaking down proteins and polysaccharides, as well as cellulose, thereby enhancing the nutritional value of ingested grains and grasses. After mixing the rumen, mushroom stems, powdered kelp, and worm castings, the matrix itself was composted for about six months, with regular turning, watering, etc., all prior to introduction of the bacteria and enzyme components. The time required for composting was inconveniently long and the mixture was quite complicated. Thus, this matrix was very expensive to manufacture.

From the above description of two effective organic matrices, it will be obvious that other modifications of the organic matrix will be effective so long as the COD is low, namely less than about 10,000 mg/kg. Other composts and like matrices having a suitably low COD of about 10,000 mg/kg or less could be prepared by more extensive composting or deliberate introduction of other fungi or microbial decomposers. However, complete elimination of the organic matrix adversely affects the efficacy of the blend in treatments of waste materials or contaminants.

Tests were conducted to determine the efficacy of either the nutrient source or the enzyme/bacteria blend alone. In these tests, three treatments of sewage sludge to measure TSS reduction and three treatments of a nutrient broth to measure COD reduction were run in parallel. One treatment used fiberglass as a bulking agent in lieu of the nutrient source with the enzyme/bacteria blend of Dry Blend A. The second treatment used the nutrient source of Dry Blend A without the enzyme/bacteria blend. The third treatment used the combination of the nutrient source with the enzyme/bacteria blend which comprises Dry Blend A. The three various blends were activated in potable fresh water for twenty-four hours at 90° F. The "activated" blends were then added to flasks containing, as indicated below, either a nutrient broth made from dried cat food or sewage sludge and incubated for 24 hours.

| Treatment of Nutrient Broth | |
| --- | --- |
| Sample | COD |

| | |
|---|---|
| Control (no treatment) | 3,760 mg/L |
| Dry Blend A | 2,840 mg/L |
| Mushroom Compost, No Enzymes | 3,160 mg/L |
| Enzyme Premix & Fiberglass, No Compost | 3,420 mg/L |

| Treatment of Sewage Sludge | |
|---|---|
| Sample | TSS |
| Control (no treatment) | 34,050 mg/L |
| Dry Blend A | 23,850 mg/L |
| Mushroom Compost, No Enzymes | 24,650 mg/L |
| Enzyme Premix & Fiberglass, No Compost | 25,250 mg/L |

Although all three treatments reduced the COD or TSS, the treatment with Dry Blend A reduced the COD or TSS over either of the treatments missing a component. This demonstrates that neither the enzymes and bacteria nor any microbes or enzymes still in the mushroom compost are alone sufficient to reduce the COD or TSS to the levels seen in the combination treatment in 24 hours.

In accordance with the sewage treatment aspect of the present invention, a quantity of Dry Blend A or Dry Blend B is activated by suspending a porous sack containing it in an activation tank 50 with a relatively small volume of water. Although relatively pure water is preferred, "contaminated" water having a BOD of less than about 200 to 300 mg/L may be used and may be considered as "fresh" water. The activation continues for about six to forty-eight hours, without deliberate aeration, resulting in an activated solution. The duration of the activation depends on the water temperature. When the water temperature is about 90° F. to about 95° F., then activation can occur quickly, often in about six hours. However, when the water temperature is no more than about 60° F., considerably more time is required for activation, namely up to forty-eight hours.

It is believed that activation allows the microbes present in the dry blend to begin active growth and division, using the available contained nutrients, some of which, it is believed, may have stimulatory powers beyond serving as a mere food source.

Once activation is completed, the activated solution is introduced to a larger volume of liquid sludge, such as from a digester, for acclimation in an acclimation tank 60. The introduction of the activated solution to the volume of sludge for acclimation may occur in the same container as the activation. However, the preferred embodiment involves transferring the activated solution to another, larger tank 60 and introducing the volume of sludge to this tank, as through 4" pipes fitted to enable transfer of the various materials from tank to tank.

Just as in the activation, the length of time required for acclimation will vary depending on the temperature of the acclimating solution, as well as on factors such as the convenience of the workers, taking into account the day of the week. Acclimation usually continues for from about six to about forty-eight hours, and preferably overnight. During acclimation, the microbes originally present in the dry blend are believed to continue their active growth and division. It is believed that acclimation quickly achieves logarithmic growth rates. Some adaptation to the particular sludge components may also occur through selection mechanisms.

Once acclimation is deemed complete, an aliquot of the acclimated solution, ranging from 85% to 90%, but preferably about 90%, is transferred to the digester 30 to inoculate the sludge in the digester. The remainder of the acclimated solution, a residual amount ranging from 15% to 10%, is optionally usable in a repetition of the acclimation step described above. In the repeated acclimation, additional sludge and additional activated solution, prepared as described above, should be added to the remainder of the previously acclimated solution.

After the microbes and enzymes in the acclimated solution are introduced into the digester, the sludge begins to rapidly degrade. The inoculated sludge is held in the digester to treat the TSS for at least two days and, preferably for seven days or more, at customary digester temperatures, preferably in the range of about 90° to 100° F. The degradation is generally anaerobic, with no need for aeration. In the preferred embodiment, aeration is minimized, permitting the more inefficient anaerobic digestion to proceed.

Anaerobic digestion is inherently inefficient. As anaerobic microbes feed on the nutrients in the sludge, they synthesize less cellular mass than aerobic microbes do. Unfortunately, this very inefficiency means that anaerobic digestion is typically very slow. Even large digesters with extended retention times using prior art methods do not degrade the organic material to insignificant amounts.

If the rate of anaerobic digestion were to be increased, then the suspended solids could be reduced enough in mass so that the suspended solids could be recycled through the plant in the same fashion as the supernatant. Given enough passes through the plant, the suspended solids could decrease so much in amount as to significantly affect the tonnage of solids to be disposed of. Exemplary of this is a sewage treatment plant that receives 1,000,000 gallons (about 3,800,000 liters) of wastewater per day with an initial influent TSS of 250 mg/L. In this hypothetical, after passage of the influent through a primary clarifier 20, a stream of sludge is created which is pumped to a digester 30 of approximately 4,000 gallons (15,200 L) with a TSS of 40,000 mg/L. Typical prior art digestion might reduce this to 20,000 mg/L. If the contents of the digester were to be recycled through the plant such as by reintroducing it in the clarifiers 20, it would increase TSS from 250 mg/L to 327 mg/L, imposing an excessive solids loading on the plant. Digestion using the present procedure can, however, reduce the TSS in the digester to 1,000 mg/L and lower. If this material was recycled to the clarifiers, it would increase the influent TSS insignificantly from 250 mg/L to only 252 mg/L. This increased influent load would be well within the design parameters of the plant for solids loading because these plants are already designed for some extra loading of TSS, as from the filtrate recycled from filtrate tank 70.

Because anaerobic digestion is inefficient in using energy sources, the organic molecules which are consumed by microbes are converted to $CO_2$, ammonia, methane, and water to provide energy. Very little of the organic matter is converted to cellular mass. The resulting $CO_2$, ammonia, and methane may be vented from the plant or the methane may be further combusted to $CO_2$ as an energy source, using conventional methods. Some nitrogen may also evolve as a result of denitrification.

If the TSS is reduced to less than 2,000 mg/L, the water, inorganic matter, and any organic molecules not consumed by microbes may be recycled to the front of the plant, such as to the clarifiers 20, for retreatment without significantly increasing the load on the plant. Eventually, however, enough inorganic matter will build up in the digester 30 so that it will be necessary to dewater and dispose of it and the organic material present in a filter or centrifuge 80. Alternatively, the water or supernatant may be cycled directly to the wastewater effluent treatment while the solids are dewatered and disposed of via incineration or landfill.

In the practice of the present invention, even though the organic materials are not all completely reduced to $CO_2$, methane, ammonia, and water, it is believed that their polymeric nature is considerably decreased, with the celluloses, proteins, lipids, starches, lignins, nucleic acids, hemicelluloses, and other polysaccharides and polymers being much reduced in average length by their digestion with enzymes, bacteria, and other microbial activity. This reduction in length in turn also results in reducing the colloidal nature of the organic material. Therefore, some of the water previously trapped in the colloidal organic material becomes more accessible for dewatering treatments, resulting in a cake which contains less water per volume of influent sewage, and thus in decreased total "solids" to dispose of.

In prior art methods using enzymes, some reduction of the water content of the filter cake has been observed. However, this has resulted from a decrease in the amount of water trapped in colloidal suspension. In the present invention, reduction in "solids" content in the filter cake results from very significant decreases in the organic materials present altogether (measured as volatile solids), as well as from a substantial reduction in the size of the molecules, hence the amount of water trapped in colloidal suspension.

Once the sludge in the digester has been sufficiently reduced initially, the frequency of the inoculations of the acclimated Dry Blend may be decreased in number, or the amount of the Dry Blend mixture used may be reduced so as to inexpensively maintain a steady state of lowered volume of sludge and amount of TSS in the digester. Typically 1 to 1.5 lbs dry blend per day over a 5 day/week schedule per million gallons per day (MGD) of plant is required to start. This can be reduced to about 0.5 lb dry blend per day per MGD at steady state.

The invention may be better appreciated by referring to the following examples.

EXAMPLE 1

To determine if activation and acclimation of an enzyme/microbe blend could make it economical to degrade organic solids and reduce COD in a sewage treatment application, testing occurred at the U.S. Naval Base Sewage Treatment Plant, Treasure Island, San Francisco Bay, Calif. in August and September 1994.

One half pound of Dry Blend A, containing bacteria, enzymes and used mushroom compost as described above, was placed in a porous sack. This sack was suspended for 24 hours in 8 gallons of fresh water in a 15 gallon plastic drum at ambient temperature of about 75° F. to produce an activated mixture.

After activation, the activated mixture and the sack were transferred to a 1500 gallon acclimation tank. The tank was filled with sludge from the digester. The activated mixture and sludge were allowed to acclimate for twenty-four hours at an ambient temperature to produce an acclimated mixture.

After 24 hours of treatment, about 90% (about 1300 to 1400 gallons) of the acclimated mixture was introduced into a 185,000 gallon digester to treat the sludge. The sludge content was about 160,000 gallons. The porous sack remained in the acclimation tank.

Meanwhile activation of another 0.5 pound of the enzyme/microbe blend occurred in another 8 gallons of water under the same conditions to produce another batch of activated mixture.

The newly activated mixture and enough sludge from the digester were added to the acclimation tank (and to the remaining acclimated mixture) to fill the tank.

Although the experimental design called for the activation/acclimation/treatment to occur optimally four times each week from Wednesday, Aug. 10, 1994 to Tuesday, Sep. 20, 1994, the treatments did not reach the optimum number. Nevertheless, TSS declined by August 30 as shown below. Measurements are in mg/L.

| DATE | 8/10 | 8/19 | 8/30 | 9/16 |
|---|---|---|---|---|
| Sludge TSS | | 13,970 | 11,180 | 12,475 |
| Supernatant TSS | 4,388 | | 1,375 | 3,875 |

Additionally, the volume of centrifuge filter cake shipped to a landfill declined from 2 twenty-two cubic yard debris bins per month prior to introduction of the new treatment technique to 1 such bin per month in August and September. After treatment concluded sometime after August 30, supernatant and sludge TSS began to increase as shown by the September 16 data, and the supernatant and sludge TSS eventually returned to its earlier high level, and the centrifuge cake shipment returned to 2 twenty-two cubic yard bins per month.

EXAMPLE 2

A second test occurred at the U.S. Naval Base Sewage Treatment Plant, Treasure Island, San Francisco Bay, Calif. in November and December 1994. In this test, one half pound of Dry Blend A, containing bacteria, enzymes and used mushroom compost as described above, was placed in a porous sack. This sack was suspended for 24 hours in 8 gallons of fresh water in a 15 gallon plastic drum at about 70° F. to produce an activated mixture.

After activation, the activated mixture and the sack were transferred to a 1500 gallon acclimation tank. The tank was filled with sludge from the digester. The sludge and the activated mixture were initially mixed upon introduction. The activated mixture and sludge were allowed to acclimate for twenty-four hours at an ambient temperature of about 60° F. to produce an acclimated mixture.

After 24 hours of treatment, about 90% (about 1300 to 1400 gallons) of the acclimated mixture was introduced into the 185,000 gallon digester to treat the sludge. The sludge content was about 160,000 gallons. The porous sack remained in the acclimation tank. Activation of another 0.5 pound of the enzyme/microbe blend was conducted in another 8 gallons of water under the same conditions to produce another batch of activated mixture.

The newly activated mixture and enough sludge from the digester were added to the acclimation tank (and to the remaining acclimated mixture) to substantially fill the acclimation tank.

In this case, the experimental design called for the activation/acclimation/treatment to occur optimally five times each week from Wednesday, Nov. 7, 1994 to Tuesday, Dec. 13, 1994. Again, treatments did not reach the optimal number. Nevertheless, TSS declined over time as shown below. Measurements are in mg/L.

| DATE | 11/7 | 11/16 | 11/29 | 12/13 |
|---|---|---|---|---|
| Sludge TSS | | 22,295 | 19,050 | 3,480 |
| Supernatant TSS | 15,600 | 2,075 | | 608 |

Additionally, the volume of centrifuge filter cake shipped to a landfill again declined from 2 twenty-two cubic yard debris bins per month prior to introduction of the new treatment technique to 1 such bin per month in November.

EXAMPLE 3

In January and February 1995, about two months after the second test concluded, a third test using Dry Blend A was conducted at the same Treasure Island Sewage Treatment Plant. This test was designed so a thorough mass balance could be calculated. After six weeks of treatment in the same manner described above (with activation of one-half pound to one pound of Dry Blend A, acclimation, etc. occurring 5 times each week), the following results were obtained.

The following calculations account for the solids that were treated in the digester 30 at the wastewater treatment plant at the Treasure Island US Navy Base. Loading to the plant averaged 1,125 lbs of solids per day, of which 700 lbs/day were removed to the digester 30 from the primary clarifier 20 as a 3–4% TSS solution of approximately 3,000 gallons. The volume of the digester is 185,000 gallons.

Mass balance calculations are based on the following readings of TSS in mg/L taken from the digester over the period of Jan. 23 to Mar. 8, 1995.

| Date | Sludge | Supernatant (Low Port) | Supernatant (Middle Port) | Supernatant (High Port) | Overall Arith. Average |
| --- | --- | --- | --- | --- | --- |
| 1/23 | 5,250 | 1,575 | 1,975 | 800 | 2,375 |
| 2/1 | 4,200 | 2,150 | 1,100 | * | 2,483 |
| 2/8 | 1,750 | 725 | 1,550 | * | 1,342 |
| 2/15 | 5,600 | 4,675 | 9,625 | * | 6,633 |
| 2/22 | 4,350 | 5,300 | 4,250 | * | 4,633 |
| 3/1 | 5,775 | 10,925 | 5,050 | 8,500 | 7,563 |
| 3/8 | 4,000 | 2,500 | 2,325 | 5,550 | 3,594 |

*Samples from the supernatant high port were not obtainable because increased fermentation formed a "cap" that clogged the high port.

The organic nutrient was altered from that used in Dry Blend A for experimental purposes for the period from 2/10 to 2/25. The nutrient in Dry Blend A comprised mushroom compost that had been inadvertently left in the rain and was leached as a result of weathering. This resulted in a decreased efficiency of digestion. The original Dry Blend A was restored on 2/26.

The initial TSS in the digester at the start of treatment January 23 was 2,375 mg/L. The volume of sludge in the digester was 185,000 gal or 703,000 L. Thus, the digester had about 1,670 kg or 3,670 pounds solids present at the beginning of treatment.

Over the 45 days of treatment (January 23 to March 8), about 700 pounds of solids were added daily to the digester, for a total of 31,500 pounds solids added. The total load was 35,170 pounds. Historically, this digester would reduce solids on average by 21.8%, from 35,170 pounds to 27,498 pounds.

On February 7, 43,200 gallons with a TSS of 4,200 mg/L, or 1,514 pounds solids, were transferred from the digester. On February 26, a centrifuge cake of 32,290 pounds having 21% solids, or 6,781 pounds solids, was removed. On February 3, an additional 7,200 gallons with a TSS of 5,550 mg/L, or 331 pounds solids, were transferred from the digester. Thus, the total of pounds solids removed or digested at historical rates was 8,626 pounds, leaving 18,872 pounds of solids to account for.

When the test terminated on March 8 the TSS of the 185,000 gal sludge was 3,594 mg/L. Thus, the digester had 5,558 pounds solids present at the end of treatment; 5,558 pounds is about 30% of the historical reduction to 18,872 pounds.

Additionally, the centrifuge cake was analyzed for total solids and volatile solids.

At the start of treatment January 23, the cake was 25% total solids. Of the total solids, volatile solids made up 59%. The cake removed February 25 was 21% total solids. Of the total solids, volatile solids made up only 34%.

This demonstrates that the volatile organic solids in the filter cake were reduced by almost 50%, from about 59% to about 34%. The percent water in the filter cake increased only slightly, from 75% to 79%.

This reduction both in total mass over the customary and expected total mass and the reduction in volatile solids in the centrifuge cake demonstrates the efficacy of the treatment in reducing organic solids.

Industrial waste streams other than residential sewage streams contribute at least two-thirds of the organic matter in wastewater in the United States. The EPA and state and local governments may require particular treatments and levels of TSS or BOD in the effluent leaving a plant.

In accordance with the present invention, it has been determined that streams other than sewage which carry solids and other contaminants may be advantageously similarly treated with materials having a COD of less than about 10,000 mg/kg.

Thus streams emanating from waste generators such as plants, tanneries, canneries, or mills which process or manufacture wood, pulp, paper, chemicals, petrochemicals, pharmaceuticals, textiles, glues, or foodstuffs, including milk, coffee, eggs, meat, such as beef, fish or chicken, beer, and wine may be treated with dry blend compositions as described above which comprise particular enzymes, microbes, and nutrients having a COD less than about 10,000 mg/kg.

Preferably, the process of treating such waste streams employs activation and acclimation steps like those described above in the sewage treatment plant technique, namely activation in fresh water and acclimation with a waste stream moiety. However, treatment of streams differs from treatment in contained plants, such as sewage treatment plants, in that streams may continuously flow, and do not retain wastewater to be treated over extended periods such as days.

For effective treatment to reduce organic contaminants of a stream, the acclimated mixture should be held in contact with the stream to be treated for at least about three hours, more preferably at least 24 hours. One way to do this is to use a holding tank or sump similar to the digester 30 of the sewage treatment plant embodiment. The holding tank is located in the stream between the waste generator and the downstream moieties. In addition, a significant volume, preferably more than 10%, of the stream should be recycled if the treatment is in a single pass of limited duration or distance, much as was done in the sewage treatment plant embodiment. An example of a non-sewage treatment plant is disposal of dairy waste.

EXAMPLE 4

Treatment of a dairy waste flushing system was successfully conducted using Dry Blend A in just seven days. The system to be treated, like most dairy waste flushing systems, had excess solids and foul smell. The set-up of the system involves flushing the dairy barn of dairy animal waste to a sump. In the sump, the solids and liquids are separated. The solids separation and the manure sump are somewhat similar to the clarifier 20 of the sewage plant treatment embodiment. The solids separation is done with a mechanical separator. The liquids are removed to a pond and recycled to the dairy barn to again flush the barn.

One pound of Dry Blend A was placed in a porous sack. This sack was activated in fresh water at an ambient temperature (of about 70° F.) for about 24 hours to produce an activated mixture.

After activation, the activated mixture and the sack were transferred to a 100 gallon acclimation tank. The acclimation tank was filled with the liquid transferred from a manure sump. The activated mixture and sump liquid were allowed to acclimate for about 24 hours to produce an acclimated mixture.

After 24 hours, about 90% of the acclimated mixture was added to inoculate and treat a 20,000 gallon manure sump where the solids separation occurred.

Activation, acclimation, and treatment of the manure sump was repeated five times over five days.

In addition to the treatment of the sump, the liquid separated from the solids in the manure sump was transferred to a 1.9 million gallon irrigating pond. The pond was similarly treated. Namely, one pound of Dry Blend A was activated in fresh water for 24 hours to produce an activated mixture. After activation, the activated mixture was transferred to a 2000 gallon tank which was filled with a manure slurry from the manure sump for acclimation. After acclimation for 24 hours, the acclimated mixture was pumped into the irrigating pond.

As pointed out above, the irrigation pond is used as a source for both irrigation of farmland and for flushing the dairy barns.

After treatment of the pond as described over a period of 7 days (which was preceded by treatment of the sump for five days), the following pond parameters were measured:

(1) a 73% reduction in Biological Oxygen Demand (BOD);

(2) a 92% reduction in Total Suspended Solids (mss);

(3) an 82% reduction in Total Organic Nitrogen; and (4) a 66% reduction in Total Kjeldahl Nitrogen.

Other important practical benefits of this treatment were: a dramatic reduction of manure odor from the pond; cleaner, less slippery alleys; better sand removal by sand traps with clean, reusable sand; nearly total destruction of waste grain not eaten by the cattle before the flush water went over the separator resulting in reduced separated solids and cleaner and nearly odor-free separated solids now useable for bedding. There have been these additional beneficial effects: reduction of accumulated manure solids throughout the entire flush system, unclogging drains, reducing floating and settled solids in the sump; cleaning fouled pump intakes (notably the pump used to pump pond water into the silage irrigation system); cleaning up sand deposits in the manure sump by degrading the intermixed manure making the sand "stiffer" and thus easier to scoop up, as well as easier to settle, thus preventing sand scouring of expensive pump components; and treatment has initiated the degradation of the adjacent solids-filled primary pond offering the possibility of clearing filled ponds of solids biologically without expensive excavation. The biological processes begun by the treatment continued to work for at least 2 months.

In addition to treating wastewater in sewage stream treatment plants and industrial stream wastewater, treatments of natural streams, ponds and other bodies of water may also be undertaken in accordance with the process and compositions of this invention. In this regard, treatment may be necessary in ponds in which fertilizer runoff, gasoline or oil spills, or spills of other organic compounds has adversely affected the BOD and levels of dissolved oxygen (DO), perhaps increasing algal growth.

EXAMPLE 5

In May 1994, 10,000 gallons of leachate from a silage stockpile were introduced into San Antonio Creek, Sonoma County, Calif. The flow rate of the stream was essentially zero due to lack of rain. The creek could thus be characterized as a series of ponds. The leachate directly affected four ponds in this series. After the leachate entered the creek, the dissolved oxygen (DO) was zero and the BOD was extremely high. The volume of each pond was estimated to be one acre-foot (325,000 gallons).

One pound of Dry Blend A of the present invention was placed in a porous sack. This sack was suspended in a 150-gallon drum of fresh water at ambient temperature (about 70° F.) for 24 hours to produce an activated mixture.

The activated mixture was transferred via gravity flow to a 500 gallon fiberglass feed trough. The trough was filled with leachate-contaminated water from the pond. During the next 24 hours, the water was circulated from the trough to the drum and back again in a closed loop and was maintained at a temperature of about 70° F. to produce an acclimated mixture.

After acclimation, pond treatment began. The acclimated mixture in the 500 gallon feed trough was pumped into one of the ponds and was mixed with the pond water via a second pump. Sprayers were simultaneously used to aerate the pond.

This process of activation, acclimation, and treatment continued daily over a 5 day period until the DO returned to its normal level of above 5 mg/L. This DO level was maintainable without aeration. The first pond reached a level of 5 mg/L in seven days. The other three ponds in the creek were treated sequentially in the same fashion and all of them reached 5 mg/L within 20 days.

In all, about 1.3 million gallons of leachate-contaminated water were treated with only 15 pounds of Dry Blend A.

It will be apparent to those skilled in the art that further modifications may be made without departing from the spirit and scope of the present invention. Accordingly, the claims are intended to embrace all modifications with their scope.

What is claimed is:

1. A method for the continuous biological treatment of sewage to reduce the volume of aqueous sludge in a sewage treatment plant comprising the steps of:

(A) providing a mixture comprising
  (1) active amounts of an enzyme mixture comprising amylase, lipase, protease, and cellulase;
  (2) active amounts of bacteria comprising *Bacillus subtilis* and *Pseudomonas fluorescens*; and
  (3) a nutrient source having a chemical oxygen demand of 10,000 mg/kg or less;

(B) immersing said mixture in fresh water for from about 6 hours to about 48 hours at a temperature of at least 60° F. to produce an activated mixture;

(C) mixing a volume of aqueous sludge from said sewage treatment plant with a volume of said activated mixture for from about 6 hours to about 48 hours at a temperature of at least 60° F. to produce an acclimated mixture; and (D) adding a volume of said acclimated mixture of step (C) to a sludge treatment tank in said sewage treatment plant and maintaining said mixture and said sludge in contact at a temperature of at least 60° F. for at least two days to reduce the volume of aqueous sludge and suspended solids in the sewage treatment plant.

2. The method of claim 1, and wherein step (B) is conducted without aeration.

3. The method of claim 1, and wherein steps (B) to (D) are repeated regularly to reduce and maintain a reduced volume of aqueous sludge and suspended solids in the sewage treatment plant.

4. The method of claim 1, and wherein a part of the acclimated mixture of step (C) is reserved for use; and (E) repeating steps (B) through (D) to provide additional volumes of acclimated mixture for addition to the sludge treatment tank, each time using a reserved part of an acclimated mixture for production of each additional volume of acclimated mixture.

5. The method of claim 1 wherein the volume of aqueous sludge of step (C) is taken from a sludge digester in the sewage treatment plant; and the tank in which the acclimated mixture is added to the sludge in step (D) is a sludge digester tank so that reduction of suspended solids occurs in a sludge digester tank.

6. The method of claim 1, and wherein steps (B) to (D) are repeated regularly to reduce and maintain a reduced volume of aqueous sludge and suspended solids in the sewage treatment plant.

7. The method of claim 6, and wherein steps (B) to (D) are repeated regularly to reduce and achieve a steady state reduced volume of aqueous sludge and suspended solids in the sewage treatment plant, and therefore reducing the amount of mixture used or frequency of step (D) while maintaining said steady state reduced volume.

8. The method of claim 1 wherein the temperature in step (C) is between about 90° F. and about 100° F.

9. The method of claim 1 wherein the temperature in step (D) is of at least about 90° F.

10. The method of claim 1 wherein the nutrient source comprises used mushroom compost.

11. The method of claim 1 wherein the nutrient source comprises composted cow-paunch, composted mushroom stems, powdered kelp, and worm castings.

12. The method of claim 1 wherein the method produces supernatant liquid as the suspended solids are reduced, and further comprising the step of recycling the supernatant to a sewage treatment plant clarifier.

13. A method for the continuous biological treatment of sewage to reduce the volume of aqueous sludge in a sewage treatment plant comprising the steps of:

(A) providing a mixture comprising
  (1) active amounts of an enzyme mixture comprising amylase, lipase, protease, and cellulase;
  (2) active amounts of bacteria comprising *Bacillus subtilis* and *Pseudomonas fluorescens*; and
  (3) a nutrient source having a chemical oxygen demand of 10,000 mg/kg or less;

(B) immersing said mixture in fresh water for from about 6 hours to about 48 hours at a temperature of at least 60° F. to produce an activated mixture;

(C) mixing a volume of aqueous sludge taken from a sludge digester in said sewage treatment plant with a volume of said activated mixture for from about 6 hours to about 48 hours at a temperature of at least 90° F. to produce an acclimated mixture;

(D) adding a volume of said acclimated mixture of step (C) to a sludge digester tank in said sewage treatment plant and maintaining said mixture and said sludge in contact at a temperature of at least 90° F. for at least two days to reduce the volume of aqueous sludge, hence suspended solids in the sewage treatment plant; and wherein steps (B) to (D) are repeated regularly to reduce and achieve a reduced volume of aqueous sludge and suspended solids in the sewage treatment plant.

14. The method of claim 13, and when a steady state reduced volume of aqueous sludge and suspended solids in the sewage treatment plant is achieved, thereafter reducing the amount of mixture used or frequency of step (D) while maintaining said steady state reduced volume.

15. The method of claim 13 wherein the nutrient source comprises used mushroom compost.

16. A method for the continuous biological treatment and purification of a wastewater stream containing organic contaminants comprising the steps of:

(A) providing a mixture comprising
  (1) active amounts of an enzyme mixture comprising amylase, lipase, protease, and cellulase;
  (2) active amounts of bacteria comprising *Bacillus subtilis* and *Pseudomonas fluorescens*; and
  (3) a nutrient source having a chemical oxygen demand of less than about 10,000 mg/kg;

(B) immersing said mixture in fresh water for from about 6 hours to about 48 hours at a temperature of at least 60° F. to produce an activated mixture;

(C) mixing a volume of said activated mixture with a volume of wastewater from said stream for from about 6 hours to about 48 hours at a temperature of at least about 60° F. to produce an acclimated mixture; and (D) adding acclimated mixture of step (C) to the wastewater stream and maintaining contact for at least about three hours to reduce the organic contaminants.

17. The method of claim 16 wherein the wastewater stream is generated during the processing of one of the group consisting of wood, pulp, paper, chemicals, petrochemicals, pharmaceuticals, textiles, glues, foodstuffs, milk, coffee, eggs, meat, beef, chicken, fish, beer and wine.

18. The method of claim 16, and wherein step (B) is conducted without aeration.

19. The method of claim 16 wherein the nutrient source comprises used mushroom compost.

20. The method of claim 16 wherein the nutrient source comprises composted cow-paunch, composted mushroom stems, powdered kelp, and worm castings.

21. A composition for treating waste and contaminants comprising:

an enzyme mixture comprising active amounts of amylase, lipase, protease, and cellulase;

bacteria comprising active amounts of *Bacillus subtilis* and *Pseudomonas fluorescens*; and used mushroom compost.

22. The composition of claim 21 wherein the used mushroom compost has been previously used to grow at least two crops of mushrooms.

23. The composition of claim 21 and wherein the enzyme mixture comprises at least one percent cellulase and at least one percent protease.

24. The composition of claim 21 wherein said activatable mixture is a freeze-dried mixture.

25. A method for the biological treatment and purification of a body of water containing limited dissolved oxygen and high biological oxygen demand comprising the steps of:

(A) contacting freshwater with an activatable mixture comprising an enzyme mixture comprising amylase, lipase, protease, and cellulase; bacteria comprising *Bacillus subtilis* and *Pseudomonas fluorescens*; and compost having a chemical oxygen demand of 10,000 mg/kg or less for from about 6 hours to about 48 hours to produce an activated mixture;

(B) acclimating a volume of said activated mixture with a volume of water taken from said body of water for from about 6 hours to about 48 hours at an ambient temperature to produce an acclimated mixture;

(C) adding a volume of the acclimated mixture of step (B) to the body of water; and (D) repeating steps (A) through (C) as necessary repeatedly to deliver volumes of acclimated mixtures to said body of water until the dissolved oxygen is increased and the biological oxygen demand is reduced, and they fall within predetermined acceptable levels.

26. The method of claim 25 wherein the activatable mixture is freeze-dried.

27. The method of claim 25 wherein the compost is a used mushroom compost.

* * * * *